US010667781B2

(12) United States Patent
Ikhlef et al.

(10) Patent No.: US 10,667,781 B2
(45) Date of Patent: Jun. 2, 2020

(54) REFERENCE DETECTOR NORMALIZATION USING GENERATOR CURRENT FEEDBACK

(71) Applicant: FMI Medical Systems Co., Ltd., Zhejiang (CN)

(72) Inventors: Abdelaziz Ikhlef, Hudson, OH (US); Hongbin Guo, Champaign, IL (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 184 days.

(21) Appl. No.: 15/893,010

(22) Filed: Feb. 9, 2018

(65) Prior Publication Data

US 2019/0247005 A1    Aug. 15, 2019

(51) Int. Cl.
*A61B 6/03* (2006.01)
*G01N 23/046* (2018.01)
*A61B 6/00* (2006.01)

(52) U.S. Cl.
CPC ............... *A61B 6/585* (2013.01); *A61B 6/03* (2013.01); *G01N 23/046* (2013.01); *G01N 2223/303* (2013.01); *G06T 2211/421* (2013.01)

(58) Field of Classification Search
CPC ......... A61B 6/032; A61B 6/035; A61B 6/585; A61B 6/584; A61B 6/00; G06T 2211/421; G01N 23/046; G01N 2223/303
See application file for complete search history.

(56) References Cited

U.S. PATENT DOCUMENTS

| | | | |
|---|---|---|---|
| 5,774,519 A | 6/1998 | Lindstrom et al. | |
| 6,148,057 A | 11/2000 | Urchuk et al. | |
| 2009/0046913 A1* | 2/2009 | Chandra | A61B 6/035 382/131 |
| 2015/0177386 A1* | 6/2015 | Griesmer | G01T 1/2018 250/363.03 |
| 2015/0287221 A1* | 10/2015 | Takayama | G01N 23/046 382/131 |
| 2016/0095561 A1* | 4/2016 | Tamura | A61B 6/032 378/62 |

\* cited by examiner

*Primary Examiner* — David P Porta
*Assistant Examiner* — Fani Boosalis
(74) *Attorney, Agent, or Firm* — Fishman Stewart PLLC (57) ABSTRACT

A CT system includes a rotatable gantry having an opening to receive an object to be scanned, a high-voltage generator, an x-ray tube positioned on the gantry to generate x-rays through the opening, and a pixelated detector positioned on the gantry to receive the x-rays. The system includes a computer programmed to cause the x-ray tube to generate x-rays, at a given high-voltage generator voltage (kV), toward a sub-set of detector pixels when no object is present within the opening, measure an output of the sub-set of detector pixels for a given number of views during the x-ray generation and for a total integration time, and determine a calibration factor based on the measured output and based on a generator feedback current measured during the total integration time.

20 Claims, 5 Drawing Sheets

REFERENCE DETECTOR NORMALIZATION USING GENERATOR CURRENT FEEDBACK

TECHNICAL FIELD

This disclosure relates generally to diagnostic imaging and, more particularly, to an apparatus and method of calibrating a computed tomography (CT) system.

BACKGROUND

Typically, in computed tomography (CT) imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector. Imaging data may be obtained using x-rays that are generated at a single polychromatic energy. However, some systems may obtain multi-energy images that provide additional information for generating images.

Third generation multi-slices CT scanners typically include a detector assembly having scintillator/photodiodes arrays positioned in an arc, where the focal spot is the center of the corresponding circle. The material used in these detectors generally has scintillation crystal/photodiode arrays, where the scintillation crystal absorbs x-rays and converts the absorbed energy into visible light. A photodiode is used to convert the light to an electric current. The reading is typically proportional and linear to the total energy absorbed in the scintillator.

To ensure good image quality, third generation CT scanners, and particularly detector modules within the detector assembly, should satisfy very strict specifications that include but are not necessarily limited to: a) stability of the detector over time and temperature; b) in-sensitivity to focal spot motion; and c) stable and high light output over lifetime of the detector; as examples. As such, CT scanners are typically calibrated to account for the above items.

Nevertheless, the detectors can fall out of calibration due to radiation damage to the detectors, changes in operating conditions (such as temperature) of the CT scanner, and aging of the x-ray tube, as examples. To maintain proper calibration, some known CT systems therefore include a reference detector that may be used during acquisition of CT imaging data. For instance, some existing technologies use a detector located in the x-ray tube housing or at the pre-patient collimator, and others use a detector located outside the field-of-view FOV, such as at the edges of the detector, in order to avoid blockage from the patient.

However, although such detectors may provide a convenient and readily available reference for calibration purposes, such detectors are subject to accelerated aging and damage because, being outside the FOV, they typically experience increased radiation dose, and damage can result to the reference detector during the life of the detector assembly.

Thus, there is a need to improve detector calibration in a CT system.

BRIEF DESCRIPTION

The disclosure is directed toward an apparatus, method of fabricating, and method of using a reference detector in computed tomography (CT)

A CT system includes a rotatable gantry having an opening to receive an object to be scanned, a high-voltage generator, an x-ray tube positioned on the gantry to generate x-rays passing through the opening, and a pixelated detector positioned on the gantry to receive the x-rays. The system includes a computer programmed to cause the x-ray tube to generate x-rays, at a given high-voltage (KV), toward a sub-set of detector pixels without object within the opening, an output of the sub-set of detector pixels for a given number of views during the x-ray generation and for a total integration time is measured, and a calibration factor is determined based on the measured output and based on a generator feedback current measured during the total integration time.

A method of calibrating imaging data for a computed tomography (CT) system, includes generating x-rays, at a given high-voltage generator voltage (kV), toward a sub-set of detector pixels of the CT system when no object is present within an opening of the CT system, measuring an output of the sub-set of detector pixels for a given number of views during the x-ray generation and for a total integration time, and determining a calibration factor based on the measured output and based on a generator feedback current measured during the total integration time.

A computer software system includes instructions, which, when executed generate calibration vectors to be used later in the pre-processing stage of the reconstruction image chain.

Various other features and advantages will be made apparent from the following detailed description and the drawings.

DETAILED DESCRIPTION

The operating environment of disclosed examples is described with respect to a multislice computed tomography (CT) system. Examples are described with respect to a "third generation" CT scanner, however it is contemplated that the disclosed examples are applicable to other imaging systems as well, and for CT systems having more or less than the illustrated sixty-four-slice system.

The present disclosure includes a method to substitute current reference channels used for projection data normalization by a factor based on a feedback current (mA) generated from a high voltage generator.

Figure 1:
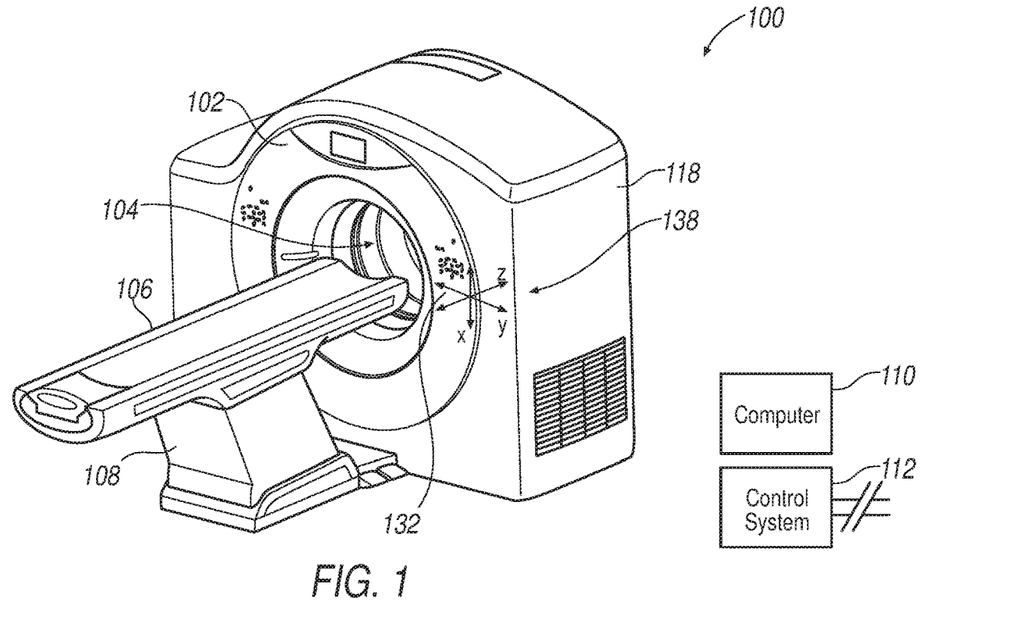
FIG. 1 is a perspective view of a CT imaging system.
Figure 2:
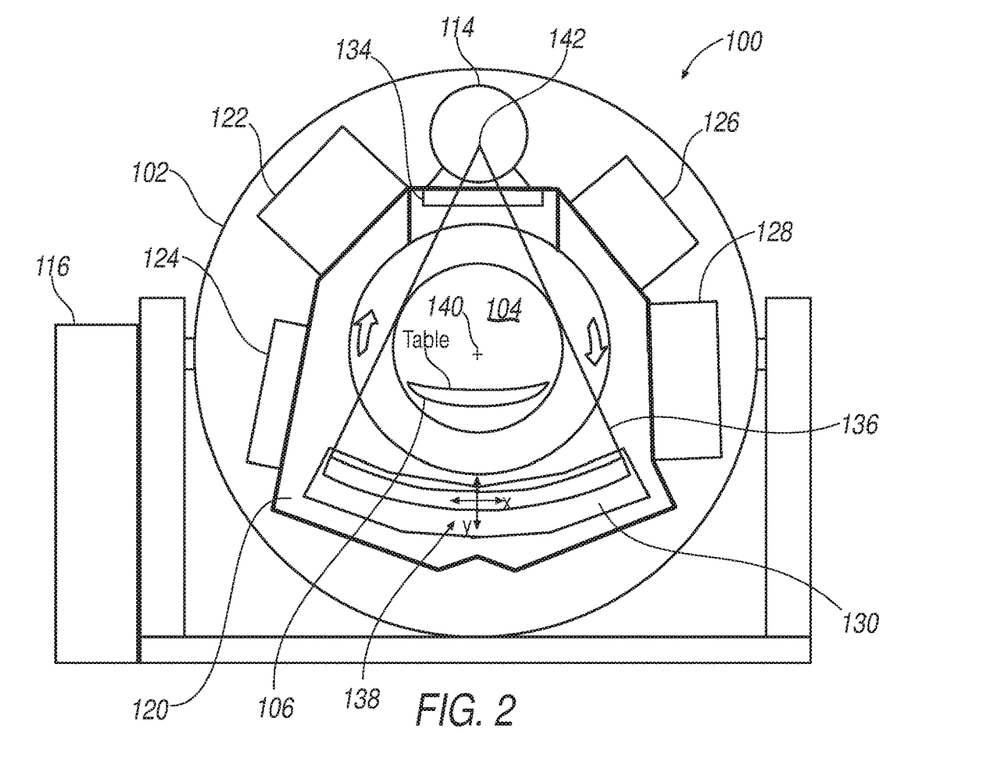
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction programs, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a high-voltage generator 128 for generating high voltage in x-ray tube 114, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is rotating about the patient, and table 106 is enabled to move the patient axially into the opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data are stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a centerpoint about which rotatable base rotates, and is an approximate position of the patient for imaging purposes). A focal spot 142 is illustrated within x-ray tube 114, which corresponds to a spot from which x-ray beam 136 emits.

Figure 3:
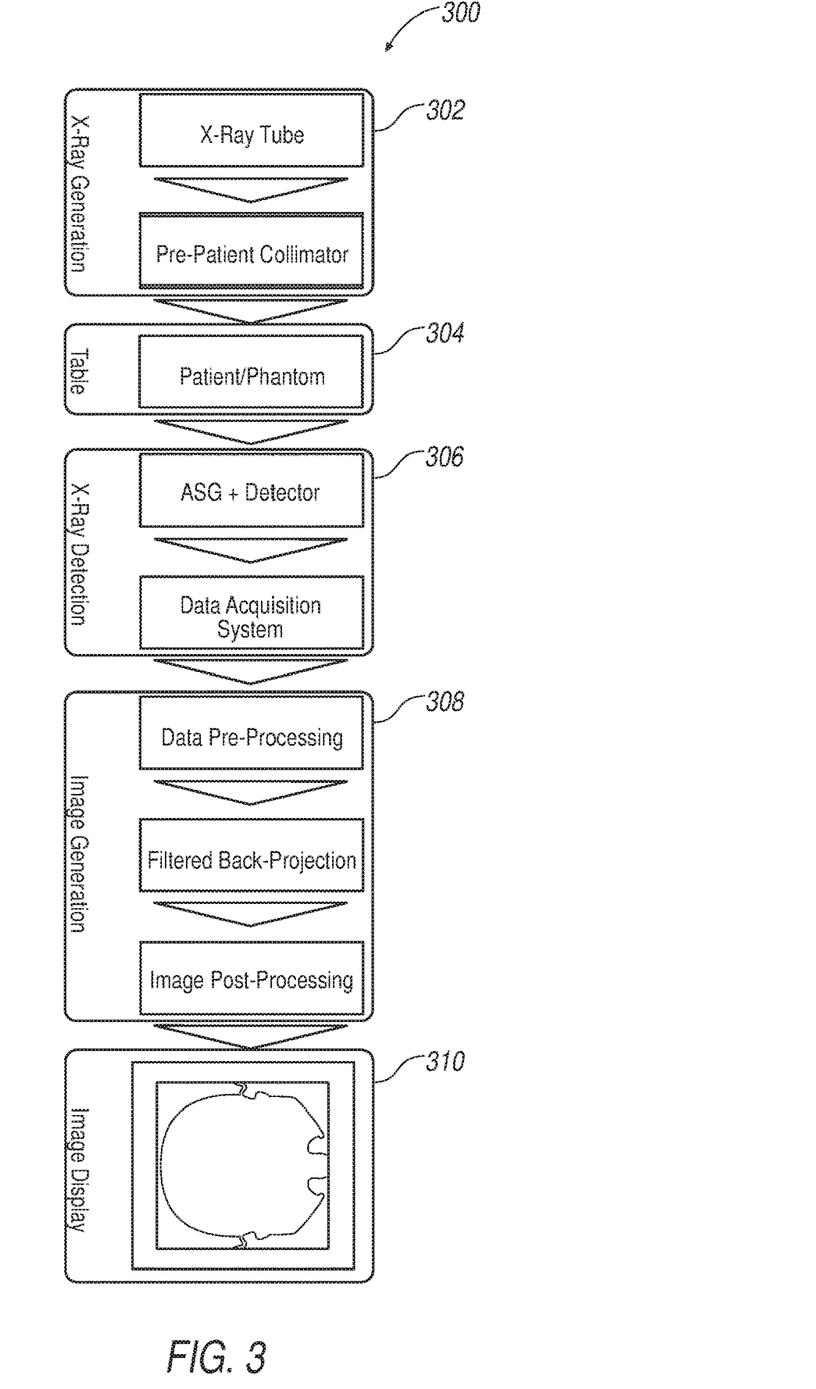
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which patient table 106 passes 304 through opening 104 of gantry 102. In one example table 106 may have a patient thereon, and in another example a phantom may be used for calibration purposes.

X-ray detection 306 occurs when x-rays having been emitted from x-ray tube 114 pass to detector assembly 130. An anti-scatter grid (ASG) prevents x-ray scatter (emitting for example from the patient as secondary x-rays and in a direction that is oblique to x-ray beam 136), by generally filtering x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slip-ring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
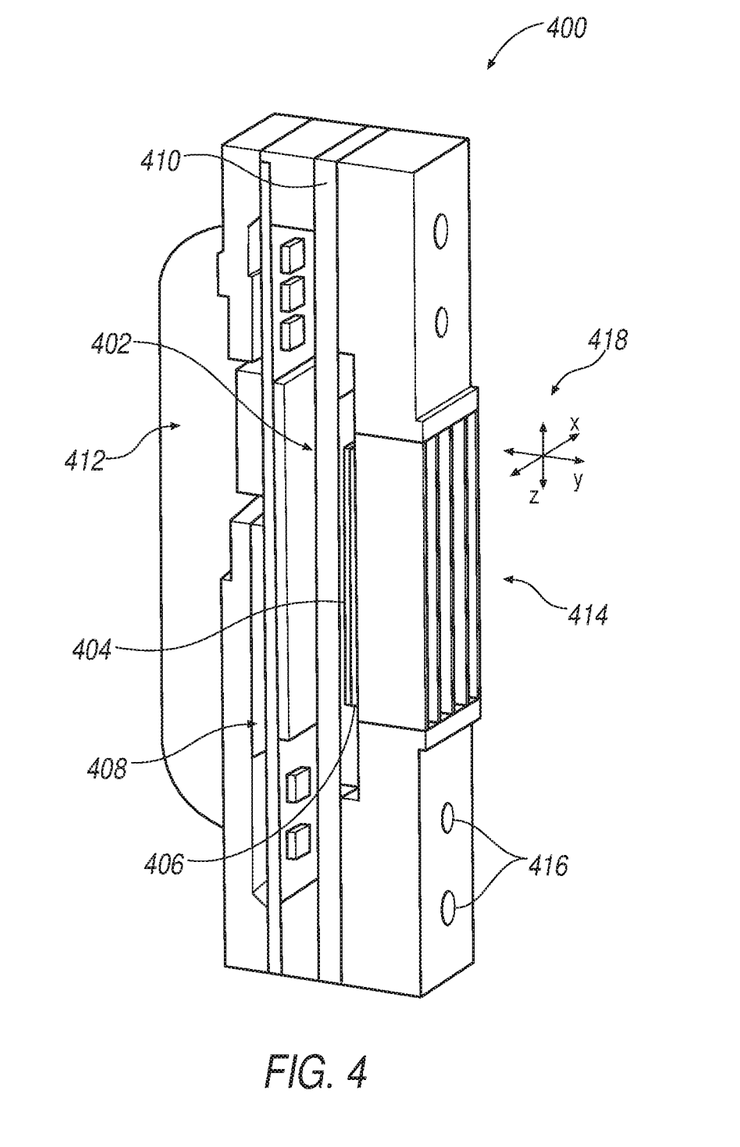
FIG. 4 is an example of a detector module.

FIG. 4 illustrates an exemplary detector module 400 that is one of a plurality of modules for use in detector assembly 130. A diode-scintillator array 402 includes a pixelated scintillator 406 positioned on a pixelated photodiode array 404. The photodiode array 404 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one embodiment, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

In CT, image formation is based on a collection of several hundred projections p, at different angles (around the object) to reconstruct an image. The projection data is the ratio of the input x-ray intensity over the output x-ray intensity followed by a logarithm operation. The projection data represents the line integral of the attenuation coefficients along the x-ray path. This equation can be represented by the ratio of the x-ray intensity after the object to the x-ray intensity before the attenuation. Because both input and output intensity profiles cannot be detected at the same time, calibration vectors are used to represent the input intensity, as shown in Eqn. 1:

$$p(ch, s, v) = -\ln\left(\frac{I_0(ch, s, v)}{I_{acal}(ch, s)}\right); \quad \text{Eqn. 1}$$

where $I_0$ is the object or output scan after being attenuated by the object and $I_{acal}$ is the air cal vectors. $I_{acal}$ is the air calibration vectors taken with no object in the beam in the same conditions. ch and s represent channel and slices. Because the x-ray intensity may vary from view to view or from calibration time to object scan time, x-rays are regularly normalized to avoid artifacts due to this variation, shown in Eqn. 2 as the formula of the projection.

$$p = -\ln\left(\frac{I_{0,norm}}{I_{aircal\_norm}}\right); \quad \text{Eqn. 2}$$

In general, the normalization of the projection data is achieved by dividing each pixel by a reference signal, provided by a detector out of field of view at every view or integration. This reference detector is typically not attenuated or blocked by the object being scanned. As stated before, some manufacturers position this detector at the tube pre-patient collimator whereas some other manufactures use some detectors located at the edges of the detector for this purpose. Equations 3-4 show the steps of normalization.

$$I_{0\_norm}(ch, s, v) = \left(\frac{I_s(ch, s, v)}{I_{ref}(v)}\right); \quad \text{Eqn. 3}$$

$$I_{aircal\_norm}(ch, s) = \left(\frac{\sum_{v=0}^{v=N} I_s(ch, s, v)/I_{ref}(v)}{N}\right); \quad \text{Eqn. 4}$$

Equation (4) represents air calibration vectors calculation method, and includes collecting N samples of the same scan conditions as the object scanning, while providing the means of the sample size. Typically, every pixel is reference normalized before the mean is calculated.

The current disclosure includes replacing the reference signal $I_{Ref}$ by a factor related to mAs (generator feedback current, i.e., the product of the tube current (mA) and the exposure time (s)) provided the x-ray fluence has sufficient current (mA) linearity. This factor is used to estimate the x-ray intensity reference for each scan settings combination. The variables of the scan include: kV, Shape Filter (also known as a bowtie filter (SF)), Focal Sport Size (FS), rotation speed (sec), and the tube current (mA). Because the x-ray signal from the tube is linear to mAs, the factor is based as f(kV,FS,SF). Because the purpose of the reference detector is to track and normalize projection data for the drift of the x-ray tube intensity, a factor based only on kV and FS (e.g., f(kV,FS) which can be updated on a daily basis.

As such, to achieve a stable and linear detector, the center of the detector is used to measure the factor for each combination of the scan where the variables are kV and FS.

In the disclosed example, there will be 8 factors: four kV values (80 kV, 100 kV, 120 kV, 140 kV), and two focal spots (small and large). By nature of third generation scanner construction, typically the centermost modules of the detector are also the most linear and stable of the system. The center modules see less attenuation from the shape filter thus yielding higher light output. In addition to the stability and higher gain, the centermost detector modules, and rows therein, will experience the least amount of radiation because there is typically an object to scan, and thus attenuate the x-ray intensity on the detector. That is, for most scanning, and regardless of object size to be scanned, the centermost modules and centermost rows of detector pixels will typically be obscured and will experience less radiation dose. For these reasons, choosing the pixels in the center area of the detector is more appropriate to provide reference vectors.

In this example, the normalization becomes as follows (by defining the following parameters):

$$R_{cal}(\text{mode}, kV, FS) = \frac{\sum_{s=s\_st}^{s=s\_end} \sum_{ch=ch\_st}^{ch=ch\_end} \sum_{v=v_{st}}^{v\_end} \text{Data}(ch, s, v)/(mA(v) \cdot T_i)}{N_s N_{ch} N_v}; \quad \text{Eqn. 5}$$

where:
$N_s$ is the number of slices (rows) (s_end−s_st) used to calculate the reference signal;
$N_{ch}$ is the number of channels (ch_end−ch_st) used to calculate the reference signal;
$N_v$ is the number of views (v_end−v_st) used to calculate the reference signal;
mode: corresponds to a detector mode of operation that may be, for instance 16×0.6 (m0) or 16×1.2 (m1) for 16 slices (in the disclosed example, but can vary for other examples and for other systems having, for instance, 64 or 256 slices, or different pixel sizes, as examples);
kV are 80 kV, 100 kV, 120 kV or 140 kV;
FS corresponds to small focal spot (SFS) or large focal spot (LFS);
mA(v) is the value of the mA current feedback from the generator at every view; and
$T_i$ is the total integration time of the view.

Accordingly, the new reference detector normalization factor $I_{Ref}(kV\ FS)$, is determined based at least in part on the generator feedback current, mAs, defined as the product of mA(v) and $T_i$ and a calibration factor $R_{cal}$.

Then, the reference is defined as follows:

$$I_{Ref}(kV,FS) = (mA(v) \cdot T_i) \cdot R_{cal}(\text{mode}, kV, FS); \quad \text{Eqn. 6.}$$

and $I_{Ref}$ is calculated for all kV's and focal spots used in the system at every view.

$R_{cal}(\text{mode},kV,FS)$ is a factor which is updated periodically and, in one example, updated every 24 hours during a daily calibration. Thus, during for instance a daily calibration, the R vectors are updated and saved in the system.

Figure 5:
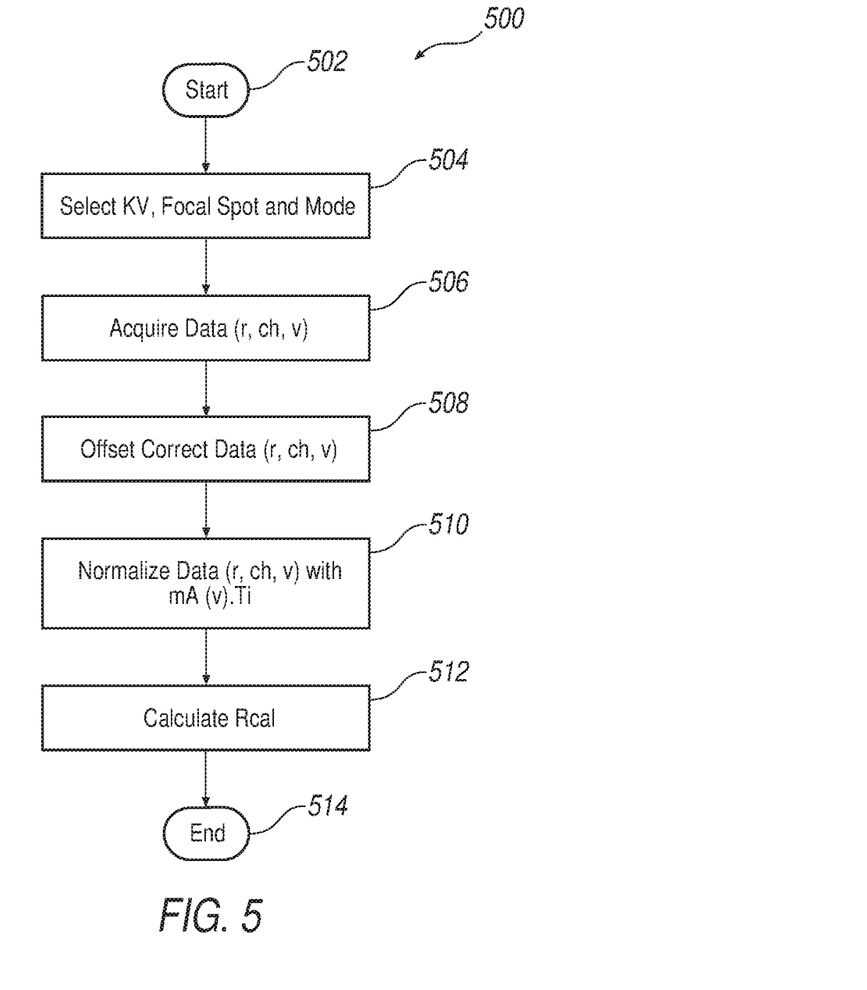
FIG. 5 illustrates a calibration process according to the present disclosure.

Referring now to FIG. 5, a calibration process 500 according to the disclosure is shown.
where:
s: slice (row)
ch; Channel
v: View In this case, every scan needs to be normalized as follows:

$$I_{norm}(ch, s, v) = \left(\frac{I(ch, s, v)}{I_{Ref}}\right) = \left(\frac{I(ch, s, v)}{(mA(v) \cdot T_i) \cdot R_{cal}(\text{mode}, kV, FS)}\right); \quad \text{Eqn. 7}$$

To calculate $R_{cal}$, channels and slices (rows) in the center of the detector are used, because these pixels will typically experience the least amount of radiation during the lifetime of the detector, making them more stable and less prone to radiation damage. Also, these channels are typically the best detectors because the specification for linearity and stability are likely more stringent in the center, as is common in third generation CT scanners.

Starting at step 502, at step 504 calibration process 500 includes selecting a kV, Focal Spot (FS), and mode, with no object or obstruction within the CT system. At step 506 data is acquired for slice (s), channel (ch), and view (v). Data is offset corrected for slice (s), channel (ch), and view (v) at step 508. At step 510 slice (s), channel (ch), and view (v)

data is normalized with mAs(v) as described in the equations above, and $R_{cal}$ is determined at step 512. Calibration process 500 ends at step 514.

Figure 6:
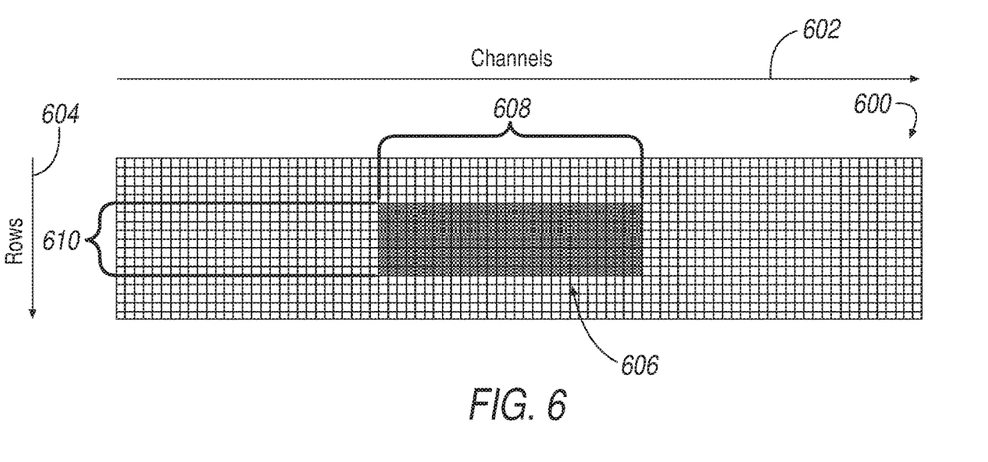
FIG. 6 illustrates an exemplary set of pixels used for $I_{Ref}$ calculation.

FIG. 6 shows an exemplary sub-set of pixels used for $R_{cal}$ calculation. Referring to FIG. 6, detector 600 may be represented by a total number of channels 602 and a total number of rows 604. A sub-set of center detectors 606 is included having a set of calibration channels 608 and a set of calibration rows (slices) 610. As can be seen in Eqn. 5 above, $R_{cal}$ is determined based at least in part on the product of $N_s$ and $N_{ch}$. In this example $N_{ch}$ corresponds with calibration channels 608 and $N_s$ corresponds with calibration rows 610. Because the product of $N_s$ and $N_{ch}$ is in the denominator of Eqn. 5, the rows and channels, $N_s$ and $N_{ch}$, used to determine $R_{cal}$ drops out of the calculation and selection of rows and channels $N_s$ and $N_{ch}$ can thereby be based on factors such as which detectors provide a stable output over time, be less prone to radiation damage, or have relatively more stringent linearity and stability.

The reference signal is calculated using the following method. For example, in a 16 slice system and according to this example, there are two modes of acquisitions (m0 corresponding 16×0.6 and m1 corresponding to 16×1.2). In this example, reference signals are measured based on the following exemplary table:

| KV | FS | Mode | Collimation Modes | Vectors (mA normalized) |
|---|---|---|---|---|
| 80 | SM | 0 | 16 × 0.6 | R(m0, 80, SFS) |
| 80 | SM | 1 | 16 × 1.2 | R(m1, 80, SFS) |
| 80 | LG | 0 | 16 × 0.6 | R(m0, 80, LFS) |
| 80 | LG | 1 | 16 × 1.2 | R(m1, 100, LFS) |
| 100 | SM | 0 | 16 × 0.6 | R(m0, 100, SFS) |
| 100 | SM | 1 | 16 × 1.2 | R(m1, 100, SFS) |
| 100 | LG | 0 | 16 × 0.6 | R(m0, 100, LFS) |
| 100 | LG | 1 | 16 × 1.2 | R(m1, 100, LFS) |
| 120 | SM | 0 | 16 × 0.6 | R(m0, 120, SFS) |
| 120 | SM | 1 | 16 × 1.2 | R(m1, 120, SFS) |
| 120 | LG | 0 | 16 × 0.6 | R(m0, 120, LFS) |
| 120 | LG | 1 | 16 × 1.2 | R(m1, 120, LFS) |
| 140 | SM | 0 | 16 × 0.6 | R(m0, 140, SFS) |
| 140 | SM | 1 | 16 × 1.2 | R(m1, 140, SFS) |
| 140 | LG | 0 | 16 × 0.6 | R(m0, 140, LFS) |
| 140 | LG | 1 | 16 × 1.2 | R(m1, 140, LFS) |

Thus, in this example, mA normalized vectors are obtained for each of the kV, Focal Spot (FS), and indicated modes. Further, it is contemplated that the above table may be updated for other systems where different modes of acquisition are used, or other parameters vary as well.

One purpose of the disclosure is to monitor the x-ray fluence of the tube and normalize the projection data to avoid artifacts that may be due to current drift of a signal from the calibration stage to the image scan or over the image scan. There are several advantages of the disclosure. In one example, there may be cost savings of detectors to perform normalization. That is, because the centermost detectors include not only the detectors that provide a stable output over time, and have relatively more stringent linearity and stability, they are also less prone to radiation damage. Thus, the cost of having separate detectors for normalization is avoided, according to the disclosure. Also, because calibration steps are performed routinely and without a patient, then potential blockage of reference detectors is avoided, which may occur because of large patient size. Further, gain variation is eliminated from one calibration state to an imaging state (temperature) over longer time for the reference detector, ensuring the use of a stable response using a frequently calibrated signal. Thus, detector operation and image quality will be more tolerant of temperature variations of the room or suite in which the CT scanner is operated.

The disclosure may be applicable to other imaging systems, as well, such as a PET system, with improvement of field of view scanning in PET where reference detectors are frequently blocked because of patient positioning issues.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A computed tomography (CT) system, comprising:
    a rotatable gantry having an opening to receive an object to be scanned;
    a high-voltage generator;
    an x-ray tube positioned on the gantry to generate x-rays through the opening;
    a pixelated detector positioned on the gantry to receive the x-rays; and
    a computer programmed to:
        cause the x-ray tube to generate x-rays, at a given high-voltage generator voltage (kV), toward a sub-set of detector pixels when no object is present within the opening;
        measure an output of the sub-set of detector pixels for a given number of views during the x-ray generation and for a total integration time; and
        determine a calibration factor based on the measured output and based on a generator feedback current measured during the total integration time.

2. The CT system of claim 1, wherein the computer is programmed to normalize projection data, obtained with an object present within the opening, using the projection data and the calibration factor.

3. The CT system of claim 1, wherein the computer is further programmed to select at least one of a kV, a focal spot size, and a detector mode of detector operation.

4. The CT system of claim 1, wherein the computer is further programmed to determine the calibration factor for more than one focal spot size.

5. The CT system of claim 1, wherein the sub-set of detector pixels includes centermost modules of the pixelated detector.

6. The CT system of claim 1, wherein the sub-set of detector pixels includes centermost rows of the pixelated detector.

7. The CT system of claim 1, wherein the computer is programmed to obtain image data for imaging an object, and normalize the image data using the calibration factor.

8. A method of calibrating imaging data for a computed tomography (CT) system, comprising:
 generating x-rays, at a given high-voltage generator voltage (kV), toward a sub-set of detector pixels of the CT system when no object is present within an opening of the CT system;
 measuring an output of the sub-set of detector pixels for a given number of views during the x-ray generation and for a total integration time; and
 determining a calibration factor based on the measured output and based on a generator feedback current measured during the total integration time.

9. The method of claim 8, further comprising normalizing projection data, obtained with an object present within the opening, using the obtained projection data and the calibration factor.

10. The method of claim 8, further comprising selecting at least one of a kV, a focal spot size, and a detector mode of detector operation for generating the x-rays.

11. The method of claim 8, further comprising determining the calibration factor for more than one focal spot size.

12. The method of claim 8, wherein the sub-set of detector pixels includes centermost modules of a pixelated detector.

13. The method of claim 8, wherein the sub-set of detector pixels includes centermost rows of the pixelated detector.

14. The method of claim 8, further comprising obtaining image data for imaging an object, and normalizing the image data using the calibration factor.

15. A computer readable storage medium having stored thereon a computer comprising instructions, which, when executed by a computer, cause the computer to:
 cause an x-ray tube to generate x-rays, at a given high-voltage generator voltage (kV), toward a sub-set of detector pixels when no object is present within an opening of a CT system;
 measure an output of the sub-set of detector pixels for a given number of views during the x-ray generation and for a total integration time; and
 determine a calibration factor based on the measured output and based on a generator feedback current measured during the total integration time.

16. The computer readable storage medium of claim 15, wherein the computer is caused to normalize projection data, obtained with an object present within the opening, using the projection data and the calibration factor.

17. The computer readable storage medium of claim 15, wherein the computer is further caused to select at least one of a kV, a focal spot size, and a detector mode of detector operation.

18. The computer readable storage medium of claim 15, wherein the computer is further caused to determine the calibration factor for more than one focal spot size.

19. The computer readable storage medium of claim 15, wherein the sub-set of detector pixels includes centermost modules of a pixelated detector.

20. The computer readable storage medium of claim 15, wherein the sub-set of detector pixels includes centermost rows of the pixelated detector.

* * * * *